United States Patent [19]

Kinzler et al.

[11] Patent Number: 5,709,998
[45] Date of Patent: Jan. 20, 1998

[54] MOLECULAR DIAGNOSIS OF FAMILIAL ADENOMATOUS POLYPOSIS

[75] Inventors: Kenneth W. Kinzler; Bert Vogelstein, both of Baltimore, Md.

[73] Assignee: The Johns Hopkins University, Baltimore, Md.

[21] Appl. No.: 169,303

[22] Filed: Dec. 15, 1993

[51] Int. Cl.$^6$ ................................................. C12Q 1/68
[52] U.S. Cl. .................... 435/6; 435/69.3; 435/172.3; 435/810; 436/501; 436/63; 536/23.1; 536/24.1; 536/24.3; 536/24.31; 536/24.32; 536/24.33; 935/77; 935/78; 935/88
[58] Field of Search .................... 435/5, 6, 69.3, 435/172.3, 810; 436/501, 63; 536/22.1, 23.1, 24.1, 24.3–24.33; 935/77, 78, 88

[56] References Cited

U.S. PATENT DOCUMENTS 5,352,775  10/1994  Albertsen et al. ............ 536/23.1

FOREIGN PATENT DOCUMENTS

| WO 89/07149 | 8/1989 | WIPO . |
| WO 91/09964 | 7/1991 | WIPO . |
| WO 92/07949 | 5/1992 | WIPO . |
| WO 93/11266 | 6/1993 | WIPO . |

OTHER PUBLICATIONS

Smith, et al., 1993, "The APC gene product in normal and tumor cells", Proc. Natl. Acad. Sci. USA, 90:2846–2850.
Zhang et al. (1989) J. Clin. Invest., vol. 83, pp. 1425–1429.
Germ-line mutations of the APC gene in 53 familial adenomatous polyposis patents; Yasuo Miyoshi, et al.; Proc. Natl. Acad. Sci. USA vol. 89, pp. 4452–4456, May 1992 Medical Sciences.
Somatic mutations of the APC gene in colorectal tumors: mutation cluster region in the APC gene; Yasuo Miyoshi, et al.; 1992 Oxford University Press; Human Molecular Genetics, Col. 1, No. 4 229–233.

Point Mutations in the dystrophin gene; Roland G. Roberts, Martin Bobrow, and David R. Bentley; Proc. Natl. Acad. Sci. USA, vol. 89, pp. 2331–2335, Mar. 1992 Genetics.

Protein truncation test (PTT) for rapid detection of translation–terminating mutations; Pauline A.M. Roest, et al.; 1993 Oxford University Press, hman molecular genetics, 1993, vol. 2, No. 10 1719–1721.

APC mutations occur early during colorectal tumorigenesis; Steven M. Powell, et al.; Nature, vol. 359, 17 Sep. 1992, pp. 235–237.

A Ligase–Mediated Gene Detection Technique, ULF Landegren, et al., Science, vol. 241, pp. 1077–1080, 1988.

Access to a Messenger RNA Sequence or Its Protein Produce Is Not Limited by Tissue or Species Specificity, Gobinda Sarkar and Steve S. Sommer, Science, vol. 244, pp. 331–334, 1989.

Molecular Diagnosis of Familial Adenomatous Polyposis, Powell, et al., New England Journal of Medicine, vol. 329, No. 27, pp. 1982–1987 (1993).

Kraus et al. (1987) The EMBO Journal, vol. 6, No. 3, pp. 605–610.

*Primary Examiner*—W. Gary Jones
*Assistant Examiner*—Ardin H. Marschel
*Attorney, Agent, or Firm*—Banner & Witcoff, Ltd.

[57] ABSTRACT

A two-pronged method for diagnosis of genetic diseases can detect mutations in about 87% of familial adenomatous polyposis (FAP) patients. One part of the diagnostic method employs in vitro protein synthesis from surrogate genes created by amplifying either cDNA or genomic DNA. The second part of the diagnostic method employs an allele-specific expression assay which distinguishes the amount of mRNA expressed in vivo from each of a patient's two alleles. These approaches are readily applicable to the diagnosis of other genetic diseases.

29 Claims, 7 Drawing Sheets

Predicted Size of Truncated APC Protein (kd)

FIG. 3A Segment 1

FIG. 3B Segment 2

FIG. 3C Segment 3

MOLECULAR DIAGNOSIS OF FAMILIAL ADENOMATOUS POLYPOSIS

The U.S. Government has a paid-up license in this invention and the right in limited circumstances to require the patent owner to license others on reasonable terms as provided for by the terms of grants CA-35494, CA-57345, and CA44688, awarded by the National Institutes of Health.

TECHNICAL FIELD OF THE INVENTION

The invention relates to the area of medical diagnostics. More particularly it relates to the area of diagnostic genetics, where the presence of mutations in certain genes presage particular disease states.

BACKGROUND OF THE INVENTION

Familial Adenomatous Polyposis (FAP) is an autosomal, dominantly-inherited syndrome characterized by the progressive development of hundreds of adenomatous colorectal polyps, some of which will inevitably progress to cancer. Although the clinical manifestations of this syndrome and its variants (e.g. Gardner's, Turcot's syndromes) have been known for many years (Bussey, H. J. R., et al. (1990) *Familial Adenomatous Polyposis*, 1-7), diagnosis still relies largely on the observation of numerous colorectal polyps developing during the second or third decade of life. Today, with FAP afflicting nearly one in eight thousand people (Alm, T. et al. (1973) *Clin. Gastroenterol*, 2:557–602) and twice that many at risk, there are over 50,000 individuals in the U.S. alone whose families could potentially benefit from genetic testing.

The first step towards genetic testing was achieved when inheritance of FAP was linked to a small region of chromosome 5(5q21) (Herrera, L., et al. (1986) *American Journal of Medical Genetics* 25:473–476; Bodmer, W. F., et al. (1987) *Nature* 328:614–616; Leppert, M., et al. (1987) 238:1411–1413). This set the groundwork for linkage studies using nearby polymorphic DNA markers. Although linkage analysis can be useful in some situations, it can benefit only a minority of FAP kindreds in practice (Petersen, G. M., et al. (1991) *Gastroenterology* 100:1658–1664; Cachon-Gonzalez, M. B., et al. (1991) *Journal of Medical Genetics* 28:681–685; Spirio, L., et al. (1993) *Am. J. Hum. Genet.* 52:286–296). Direct genetic testing became feasible when the APC gene on chromosome 5q21 was found to be mutated in the germline of FAP patients (Groden, J., et al. (1991) *Cell* 66:589–600; Joslyn, G., et al. (1991) *Cell* 66:601–613; Kinzler, K. W., et al. (1991) *Science* 253:661–665; Nishisho, I., et al. (1991) *Science* 253:665–669). Interestingly, the APC gene is also mutated frequently and early during sporadic colorectal tumorigenesis (Nishisho, I., et al. (1991) *Science* 253:665–669; Powell, S. M., et al. (1991) *Nature* 359:235–237; Miyoshi, Y., et al. (1992) *Human Molecular Genetics* 1:229–233).

Analyses of the entire coding region of APC gene have allowed demonstration of inactivating mutations in 30 to 60% of FAP patients depending on the screening method applied (Miyoshi, Y., et al. (1992) *Proc. Natl. Acad. Sci. USA* 89:4452–4456; Groden, J., et al. (1993) *Am. J. Hum. Genet.* 52:263–272; Nagase, H., et al. (1993) in press). These analyses were complicated by the varied nature of mutations which were distributed over a large portion of the APC gene, encompassing over 8,500 bp of open reading frame. Moreover, these mutations were mostly single base pair changes, small insertions or deletions. Present methods for identifying such mutations are often insensitive and always labor intensive.

There is a clear need in the art for a rapid and sensitive method for detection of APC mutations.

SUMMARY OF THE INVENTION

It is an object of the invention to provide a method for detecting mutations in an APC gene.

It is another object of the invention to provide a pair of primers for amplifying a segment of the APC gene coding sequence to form templates useful for in vitro transcription and translation.

It is still another object of the invention to provide a set of primers for amplifying all segments of the APC gene coding sequence to form templates useful for in vitro transcription and translation.

It is yet another object of the invention to provide a method for detecting mutations in any gene.

These and other objects of the invention are provided by one or more of the embodiments described below. In one embodiment of the invention a method is provided for detecting mutations in the APC gene. The method (termed herein an in vitro synthesis or IVS assay) comprises the steps of: forming APC templates by amplifying some or all portions of APC gene coding sequences in a DNA sample of a human; making a polypeptide product from said APC templates in in vitro transcription and translation reactions; analyzing said polypeptide products to determine the size of said polypeptide products, a truncated polypeptide product indicating a mutation in an APC gene in said DNA sample.

If no mutations leading to truncated polypeptides are found by the in vitro synthesized protein method described above, further steps can be taken to determine if a cis-acting mutation is present which reduces the amount of APC mRNA expressed. The method (termed herein as an allele-specific expression or ASE assay) comprises the further steps of: determining whether the patient is heterozygous for a polymorphism in the APC gene, a patient who is heterozygous having a first and a second polymorphic allele of an APC gene; and determining the relative amount of mRNA transcribed from each of said two polymorphic alleles in a DNA sample of a heterozygous patient, a ratio of mRNA transcribed from said first allele to mRNA transcribed from said second allele which is greater than 1.2 or less than 0.8 indicating a mutation in one of said alleles in the DNA. This method (ASE assay) can also be applied directly to samples without first determining an absence of truncated polypeptide products in an IVS assay.

Also provided by the present invention are a pair of primers for amplifying all or a segment of APC gene coding sequence to form templates useful for in vitro transcription and translation. One of the pair of primers comprises a transcriptional promotor and a translational initiation site. Each of the primers comprises at least about twenty contiguous nucleotides which are complementary to opposite strands of said gene coding sequence.

In another embodiment of the invention a set of primers is provided for amplifying all segments of APC gene coding sequence to form templates useful for in vitro transcription and translation. One primer in each pair of the set of primers comprises a transcriptional promotor and a translational initiation site. Each of said primers comprises at least about twenty contiguous nucleotides which are complementary to opposite strands of said gene coding sequence.

In still another embodiment of the invention a method is provided for detecting mutations in a gene. The method (an IVS assay) comprises the steps of: forming templates by amplifying some or all portions of the coding sequences of the gene in a DNA sample of a patient suspected of being affected by, or a carrier of, a disease caused by mutation in the gene; making a polypeptide product from said templates in in vitro transcription and translation reactions; analyzing said polypeptide products to determine the size of said polypeptide products, a truncated polypeptide product indicating a mutation in the gene in said DNA sample.

If no mutations leading to truncated polypeptides are found by the IVS assay described above, further steps can be taken to determine if a cis-acting mutation is present which reduces the amount of mRNA expressed from the gene. The further steps (an ASE assay) comprise: determining whether the human is heterozygous for a polymorphism in the gene, a human who is heterozygous having a first and a second polymorphic allele of the gene; determining the relative amount of mRNA transcribed from each of said two polymorphic alleles in a DNA sample of a heterozygous patient, a ratio of mRNA transcribed from said first allele to mRNA transcribed from said second allele which is greater than 1.2 or less than 0.8 indicating a mutation in one of said alleles in the DNA sample. The ASE assay can be performed even if an IVS assay has not first been performed to reveal truncated polypeptide products.

The present invention thus provides the art with a practical and sensitive screening method for detecting mutations in large genes, such as APC, which are otherwise difficult to determine absent extremely labor-intensive efforts. The invention allows routine preclinical testing of at-risk individuals, as well as genetic confirmation of de novo cases. Such methods will improve management of patients and potentiate the development of effective non-invasive preventative measures.

BRIEF DESCRIPTION OF THE DRAWINGS

FIGS. 1A and 1B show schematics of the in vitro synthesis (IVS) and allele-specific expression (ASE) assays.

FIG. 1A shows a schematic illustrating the principles of the IVS assay. The APC gene is divided into five overlapping segments encompassing the entire coding region of the APC gene. These regions are amplified using specially designed PCR primers which place the necessary transcriptional and translational regulatory sequences at the 5' end of the PCR product. Radiolabeled polypeptide is synthesized in vitro from these surrogate genes in a simple one-step coupled transcription-translation reaction (illustrated as two steps). Truncating mutations can then be identified as smaller polypeptide products after gel electrophoresis and autoradiography. The stop codon represents a typical truncating APC mutation, for example, a single base-pair change that creates a premature translation termination codon.

FIG. 1B is a schematic which shows an allele-specific-expression assay. Every normal cell has two copies of the APC gene that are identical except for occasional polymorphisms of a single base pair (cytosine [C] or thymidine [T] in this example). Normally, both alleles of the APC gene are equally represented in the RNA fraction of the cell. However, some cases of familial adenomatous polyposis are caused by mutations that lead to reduced levels of normal APC transcript from one allele. This results in an imbalance in the representation of the transcripts from the two alleles. This altered allele ratio in RNA can be detected with the allele-specific-expression assay (which is described below the dotted line). First, RNA is isolated from peripheral blood mononuclear cells. APC transcripts are converted to complementary DNA and amplified by reverse transcriptase PCR. The PCR products are then annealed with a common 9-bp oligomer and two different-sized allele-specific oligomers (8 and 10 bp). After ligation, these oligomers will yield 17-bp and 19-bp products corresponding to alleles A and B that can be distinguished by gel electrophoresis. The box shows the expected results from a normal subject and from a patient with familial adenomatous polyposis who has a mutation that leads to the reduced expression of the normal transcripts of allele A.

FIGS. 2A and 2B show IVS polypeptide analysis for detection of known truncating APC mutations.

Representative samples of FAP subjects demonstrating truncated APC polypeptides (indicated by a + at bottom and by an asterisk next to the bands) in segment 1 (S1), segment 2 (S2), and segment 3 (S3). The normal-sized, full-length APC protein (indicated at left by N) from the remaining unaltered APC allele is noted as well as background bands (also labelled N) which were noted in all lanes. The background bands probably result from internal initiation of protein translation. FAP subjects without a demonstrable truncated APC protein in the segments analyzed are also shown (Indicated by a − at the bottom).

Defined amounts of RNA, each homozygous for one allele (A or B) at the exon 11 polymorphic site, were used as templates for amplification and subsequent ligation reactions. The input ratio for each allele is shown below FIG. 4A. A linear correlation between input and the observed result in the ASE assay is apparent from FIG. 4A and the graph (FIG. 4B). The correlation coefficient, r, was 0.997.

Significantly reduced amounts of expression from an APC allele were detected in three FAP patients using ASE analysis with the exon 11 polymorphism. The "Genomic" bar indicates the average allele ratio derived from assays of 28 genomic DNA samples from 21 different individuals. The "Normal" bar indicates the average allele ratio observed in eleven RNA samples from four different individuals. The "FAP #11", "FAP #38", and "FAP #62" bars represent analysis of RNA samples from three different FAP patients. The ratio for each patient was derived from four assays. Means and standard deviations are indicated by the box and overlying brackets, respectively.

DETAILED DESCRIPTION OF THE PREFERRED EMBODIMENTS

It is a discovery of the present invention that inactivating mutations in large genes can be directly identified by a practical molecular genetic approach. The approach disclosed here has several advantages over currently available genetic methods. Although useful, genetic linkage analysis cannot be applied in individuals where kindreds are small, requisite affected kindred members are not available, or polymorphic markers are uninformative. Furthermore, linkage analysis cannot be applied when a de novo mutation is suspected. Indeed, de novo cases account for approximately one third of FAP cases (Bulow, S. (1986) *Dis. Colon Rectum* 29:102–7) and accounted for 14 of the cases in this study, 12 of which displayed APC mutations by our analysis. Additionally, because linkage analysis is indirect, some degree of uncertainty always remains.

Several studies have described the direct detection of APC mutations in FAP patients with detection rates ranging from 10 to 60% depending on the method applied (Groden, J., et al. (1991) *Cell* 66:589–600; Miyoshi, Y., et al. (1992) *Proc. Natl. Acad. Sci. USA* 89:4452–4456; Groden, J., et al. (1993) *Am. J. Hum. Genet.* 52:263–272; Nagase, H., et al. (1993) *Human Mutation* (in press); Fodde, R., et al. (1992) *Genomics* 13:1162–1168; Cottrell, S., et al. (1992) *Lancet* 340:626–630; Olschwang, S., et al. (1993) *Am. J. Hum. Genet.* 52:273–279; Varesco, L., et al. (1993) *Am. J. Hum. Genet.* 52:280–285). The screening methods employed were generally very labor intensive and could miss a substantial fraction of subtle single base pair changes. In many cases the entire APC gene was not examined, presumably due to practical considerations related to its large size. Western blot analysis has been used to detect truncated APC polypeptides and can be useful in some cases (Smith, K. J., et al. (1993) *Proc. Natl. Acad. Sci. USA* (in press)). However, many of the truncated APC polypeptides in FAP are unstable in vivo, precluding their demonstration by Western blot assays (Smith, K. J., et al. (1993) *Proc. Natl. Acad. Sci. USA* (in press)). For example, truncated APC polypeptides could not be identified in three of seven FAP cases examined by Western blot analysis, but mutations in all seven cases were easily detectable through the present approach.

Analysis of polypeptide synthesized from surrogate APC genes can rapidly identify mutations which result in truncated APC polypeptide, whether caused by splicing mutations, point mutations, or frameshifts. Likewise, ASE analysis identifies cis-acting mutations which alter APC expression, observed as an imbalance in the representation of alleles at the RNA transcript level. A variety of events including promotor mutations, splicing mutations, mutations altering transcript stability, and even imprinting abnormalities have the potential to be detected by this analysis. These molecular approaches are applicable to the identification of mutations that lead to shortened polypeptides or reduced expression in any gene, but are especially useful in analysis of large genes where conventional methods are too labor intensive. For example, most mutations in the recently isolated genes responsible for neurofibromatosis type 2 (Trofatter, J. A., et al. (1993) *Cell* 72:791; Rouleau, G. A., et al. (1993) *Nature* 363:515) and von Hippel-Lindau disease (Latif, F., et al. (1993) *Science* 260:1317) can be detected by our assays. Similarly most mutations in cystic fibrosis can be detected by these assays.

The detection of APC alterations in 87% of FAP patients illustrates the usefulness of this approach as a genetic test for FAP. Moreover, the ability to use the assay for prenatal diagnosis could be important to FAP patients planning a family. In providing a test for routine presymptomatic testing, our assays provide significant practical benefits for FAP kindreds. Registry records for the 54 positive patients show that there are at least 280 relatives at risk for FAP who can now be tested. One hundred sixty-six of these individuals are under the age of 20 and stand to gain the most from this analysis. Individuals who test positive can at least be spared the anxiety associated with disease uncertainty and can benefit from improved management. Early diagnosis should ensure that appropriate preventative measures are taken well before the inevitable development of colorectal cancers. The importance of preclinical testing is further heightened by recent studies showing promise in the pharmacologic treatment of polyposis (Waddell, W. R., et al. (1983) *Journal of Surgical Oncology* 24:83–87; Waddell, W. R., et al. (1989) *American Journal of Surgery* 157:175–179; Rigau, J., et al. (1991) *Annals of Internal Medicine* 115:952–954; Labayle, D., et al. (1991) *Gastroenterology* 101:635–639; Giardiello, F. M., et al. (1993) *New England Journal of Medicine* 328:1313). Such treatment of individuals who have inherited a mutated APC gene should be more efficacious if provided as a preventative measure before polyps or other clinical manifestations appear.

According to one aspect of the present invention, specific gene coding sequences are amplified. This can be done with any technique known in the art, including polymerase chain reaction (Saiki et al., *Science* 329:487–491, 1988), and ligase chain reaction (Wu et al. *Genomics*, 4:560–569,1989). Gene coding sequences can be amplified using reverse transcription of mRNA to form a cDNA template, or by using portions of genomic sequences which are free of intervening sequences.

DNA samples for testing may be obtained from particularly affected tissues, such as colorectal tumors, or from other tissues, such as peripheral blood, chorionic villi, and blastomeres of pre-implantation embryos. DNA samples are obtained from persons who are suspected of being affected by, or of being a carrier of, a disease which is caused by mutation of the gene to be tested. For example, a DNA sample would be obtained from a person at risk of having familial adenomatous polyposis to test for mutations in the APC gene.

Templates which are formed by the amplification of portions of the desired gene preferably will contain a transcriptional promotor and a translational initiation site. These are conveniently attached to the template during amplification by incorporating such sequences on the amplification primer which is complementary to the antisense strand of the gene. Alternatively, these can be attached by a separate ligation reaction. Upon transcription and translation of the amplified DNA (templates), a polypeptide is produced which contains all or a portion of the amino acid sequence of the gene being tested. In vitro transcription and translation (IVS) can be accomplished in any convenient system known in the art, including rabbit reticulocyte lysates and wheat germ lysates.

Polypeptides which are produced in the IVS are typically labeled with a radioactive substance or a fluorescent substance. For example, $^{35}$S-methionine can be used as a substrate during the IVS to produce radiolabeled products which can be separated on an SDS-polyacrylamide gel and autoradiographed. Other means for size separation or detection of polypeptide products as are known in the art may also be used. Mutations which are detectable by the IVS technique are those which lead to truncated polypeptides, which include nonsense and frameshift mutations.

If no truncated polypeptide products are detected by the IVS assay, one can test for mutations which cause a reduced amount of expression. According to the method of the present invention, this can be done if the patient is determined to be heterozygous for a polymorphism in the gene being investigated. Certain polymorphisms are already known in the art and can be used for this purpose, but others may be used as found. Coding change "silent" polymorphisms (i.e., those without apparent effect on gene expression or protein function) are known in APC codons 486, 545, 1493, 1756, 1960, 1678, and 2568. See Powell et al, *Nature* 359:235–237, 1992, the disclosure of which is expressly incorporated herein. The presence of such polymorphisms in the patient can be assessed, inter alia, by using the ligase-mediated gene detection technique, generally as taught by Ladegren et al., *Science* 241:1077–1080, 1988, the disclosure of which is expressly incorporated herein. The template for such a ligase-mediated reaction can be genomic DNA.

If the patient is found to be heterozygous for one or more of the polymorphisms, then the patient's mRNA can be used as a template in a second ligase-mediated assay. The relative amount of mRNA transcribed from each of the two polymorphic alleles in the DNA sample of the patient can be determined. If the ratio is more than 1.2 or less than 0.8, then a mutation is indicated in one of the two polymorphic alleles which affects the expression of the gene. Such mutations include such cis acting mutations as promotor mutations and splice site mutations.

An allele-specific ligation assay anneals two oligonucleotides immediately adjacent to each other on a complementary target DNA molecule. Two versions of the adjacent oligonucleotide are joined covalently by the action of a DNA ligase, provided that the nucleotides at the junction are correctly base-paired. One of the two oligonucleotides to be ligated is labeled. This oligonucleotide is complementary to DNA immediately adjacent to the polymorphism. The second and a third oligonucleotides are not labeled, and each of these contains as its terminal nucleotide (adjacent to the first oligonucleotide when annealed) one of the two polymorphic variants relevant to the patient under evaluation. The lengths of the two versions of the second oligonucleotide are distinct from each other. Thus, when hybridized to the complementary target cDNA molecules and ligated, the products of the ligation reaction will be distinguishable on the basis of size. The amount of the ligation products will be proportional to the amount of mRNA which was expressed in the sample from each allele. The ligation products can be separated on sequencing gels, for example, and the amount of each product determined with a phosphor imager. If the ratio of mRNA made from one allele to mRNA made from the other is outside of the range of 1+/−0.2, a mutation is indicated.

Large genes are particularly suitable for the present analysis, although it can be applied to any gene. Diseases caused by truncating-type mutations are preferred. These include, but are not limited to, cystic fibrosis, yon Hippel-Lindau disease, familial adenomatous polyposis, Hereditary Non-Polyposis Colon Cancer (HNPCC), and neurofibromatosis type 2.

Primers are provided for amplification of particular portions or entire genes. These primers are paired, and can be used as individual pairs or as sets which will amplify a whole coding sequence. Each primer is typically ten or more bases in length. The sequence of the primer is primarily complementary to one strand of the gene coding sequence, preferably about fifteen or twenty contiguous bases of the gene coding sequence. Each primer of a pair hybridizes and is complementary to opposite strands of the coding sequence. Desirably one primer of each pair will incorporate the sequence of a promoter and translational initiation sequence. This primer is complementary to the antisense strand of the gene to be amplified. Any promotor and initiation sequence can be used, that are compatible with the IVS system to be used. One preferred promotor and initiation sequence is that of T7. Others as are known in the art can be used.

EXAMPLES

Example 1

This example demonstrates that the in vitro synthesized (IVS) protein assay is a valid way to detect truncating mutations.

Figure 2A:
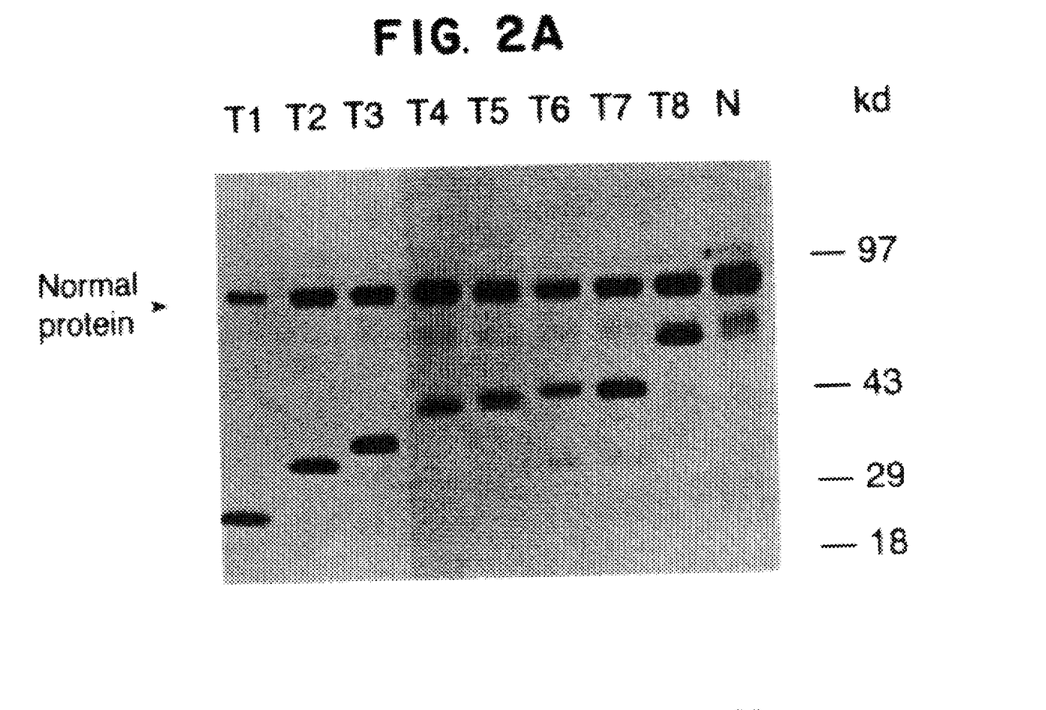
FIG. 2A shows representative IVS polypeptide samples of sporadic colorectal tumors (T1–T8), known to have truncating mutations from sequence analysis, run on SDS-PAGE. Each demonstrates the expected truncated APC polypeptide in segment 3. A significant amount of normal, full sized APC protein (Indicated at left by N) is noted from the remaining normal alleles. A normal tissue sample (Indicated by an N at top) is also shown.
Figure 2B:
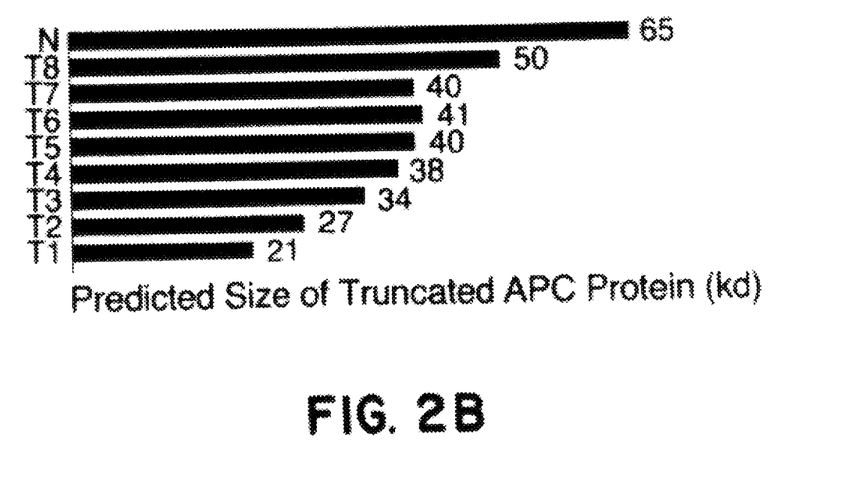
FIG. 2B graphically depicts the predicted size of truncated APC polypeptides in each of the tumors, based on sequence analysis of the APC gene.

We analyzed 20 sporadic colorectal tumors which had previously been shown to have truncating APC mutations by sequence analysis (Powell, S. M., et al. (1991) *Nature* 359:235–237). In each case, a specific truncated polypeptide corresponding to the size of the predicted mutant product could easily be identified (examples in FIG. 2). The full length protein product from the remaining normal allele was also noted in each case.

In vitro Synthesized (IVS) Protein Assay

Figure 6:
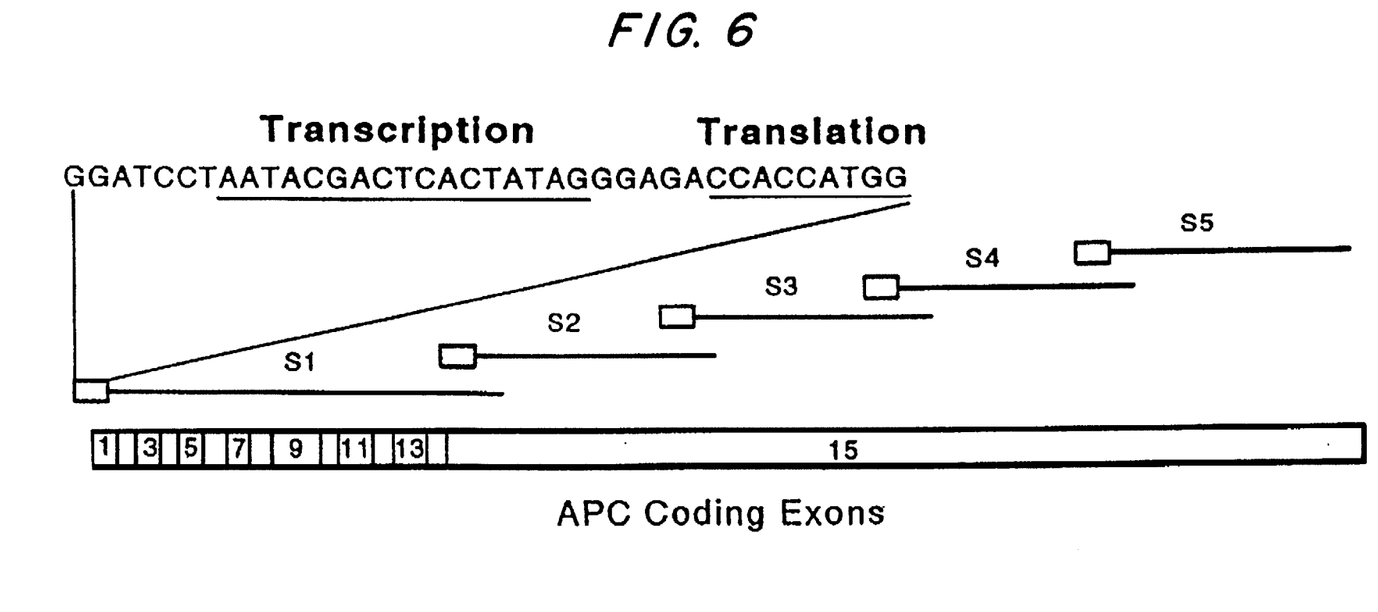
FIG. 6 shows the segments of APC used for analysis, as mapped to the APC exons.

For the purposes of PCR, the APC gene was divided into five overlapping segments (#1 to 5) containing codons 1 to 804, 686 to 1217, 1099 to 1693, 1555 to 2256, and 2131 to 2843 of APC, respectively (see FIG. 6). The primers used for PCR amplification were designed to introduce a T7 promotor sequence for initiation of transcription by T7 RNA polymerase as well as a consensus sequence for translation initiation (Kozak, M. (1987) *Nucleic Acids Research* 15:8125–8133). Segment 1 was isolated from cDNA templates prepared by reverse transcribing mRNA. Segments 2 to 5 were isolated directly from genomic DNA. For segment 1, randomly primed cDNA template was prepared by incubating 5 µg of total RNA, 1 µg of random hexamer, 1 µl of amplification enhancer (0.5 units/µL; USB) and 300 units of superscript II reverse transcriptase (BRL) in 20 µl of reaction buffer for one hour at 37 degrees. As a control for contamination, a mock reverse transcriptase reaction including everything except the enzyme was performed in parallel and used as a PCR template. Two-stage, nested PCR was performed using the USB Bind-Aid amplification kit according to manufacturer's instructions with the following changes. For the first stage, 4 µl of cDNA template, 35 ng of each outside primer (see below), and 2.5 units of Taq polymerase (Cetus) were used in a 20 µl PCR reaction for 10 cycles (95° C.×30', 62.5° C.×2', 70° C.×3') in a total volume of 50 µl.

For segments 2–5, 100 ng of genomic DNA, 350 ng each of the appropriate primers (see below), and 5.0 units of Taq polymerase were used in a 50 µl Bind-Aid amplification kit (USB) reaction. Amplification was performed for 35 cycles of 30" denaturation (95° C.), 90" annealing (segment 2, 60° C.; segment 3, 65° C.; segment 4, 62.5° C., segment 5, 60° C. and 90" extension (70° C.). All PCR reactions included a 5 minute extension period.

PCR products were used directly (without purification) as templates in 25 µl coupled transcription-translation reactions (Promega) containing 40 µCi of $S^{35}$-Methionine translabel (ICN) for one hour at 30° C. Samples were diluted in sample buffer, boiled for 5', and one tenth analyzed on 10%–20% gradient SDS-poly acrylamide gel. Polypeptides were visualized by fluorography after impregnating the gel with ENHANCE (NEN). The sequence of amplification primers were as follows with [T7-trans] (SEQ ID NO:23 representing the sequence displayed in FIG. 6:

Segment 1

External: 5'-CAAGGGTAGCCAAGGATGGC-3' SEQ ID NO: 11 and
5'-TTGCTAGACCAATTCCGCG-3' SEQ ID NO: 12
Internal: 5'-[T7-trans]-CTGCAGCTTCATATGATC-3' (SEQ ID NO: 1) and
5'-CTGACCTATTATCATCATGTCG-3' (SEQ ID NO: 2)
Segment 2: 5'-[T7-trans]-ATGCATGTGGAACTTTGTGG-3' (SEQ ID NO: 3) and
5'-GAGGATCCATTAGATGAAGGTGTGGACG-3' (SEQ ID NO: 4)
Segment 3: 5'-[T7-trans]-TTTCTCCATACAGGTCACGG-3' (SEQ ID NO: 5) and
5'-GGAGGATCCTGTAGGAATGGTATCTCG-3' (SEQ ID NO: 6)
Segment 4: 5'-[T7-trans]-AAAACCAAGAGAAAGAGGCAG-3' (SEQ ID NO: 7) and
5'-TTCACTAGGGCTTTTGGAGGC-3' (SEQ ID NO: 8)
Segment 5: 5'-[T7-trans]-GTTTATCTAGACAAGCTTCG-3' (SEQ ID NO: 9) and
5'-GGAGTGGATCCCAAAATAAGACC-3' (SEQ ID NO: 10)

Example 2

This example demonstrates that the IVS protein assay can be used to diagnose FAP from peripheral blood samples.

Figure 3A:
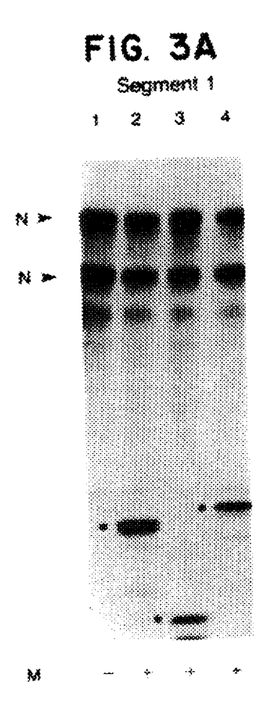
FIGS. 3A, 3B and 3C show IVS protein analysis for detection of APC mutations in FAP patients.
Figure 3B:
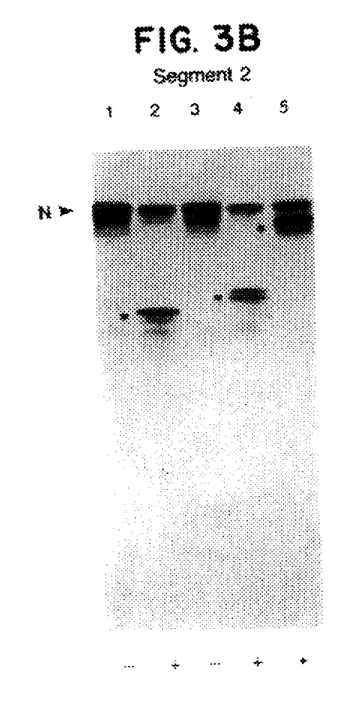
Figure 3C:
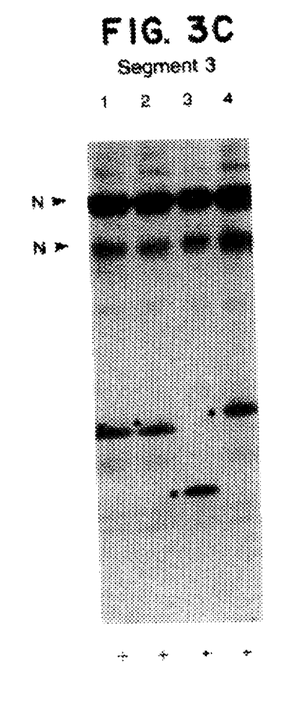

Analysis of the entire coding region of APC with the IVS protein assay identified truncating mutations in 51 (82%) patients (examples in FIG. 3). The 51 mutations were distributed over the first four segments with 29, 10, 11 and 1 being in segments 1, 2, 3 and 4, respectively.

Study Group

The most recent 62 unrelated patients enrolled in the Johns Hopkins FAP registry from whom blood samples could be obtained were selected for analysis in an unbiased manner. All of these individuals were confirmed to have classic adenomatous polyposis as defined by the presence of greater than 100 colorectal polyps at time of diagnostic endoscopy, radiologic study, or examination of surgically resected colons. The adenomatous nature of the polyps was documented by histopathological analysis.

Blood samples were also collected from nine healthy individuals, age 22–43, as normal controls and from seven relatives of three FAP patients. Informed consent in accord with institutional policy was obtained from each subject prior to drawing blood samples.

Preparation of Templates

Whole blood samples were obtained from 45 FAP patients, and consisted of 20 cc EDTA anticoagulated whole blood collected and stored overnight at ambient temperature. Genomic DNA was prepared by Chelex extraction of 30 µl of whole blood as described previously (Walsh, P. S., et al. (1991) *Biotechniques* 10:507–513). RNA was isolated by the acid guanidium isothiocyanate-phenol-chloroform extraction method (Chomczynski, P., et al. (1987) *Analytical Biochemistry* 162:156–159) from peripheral mononuclear cells prepared from 10 cc of whole blood using a Histopaque-1077 (Sigma) gradient. Lymphoblastoid cell lines were obtained from 17 FAP patients by Epstein Barr virus immortalization of their lymphocytes. RNA and DNA were extracted from such cells as described (Chomczynski, P., et al. (1987) *Analytical Biochemistry* 162:156–159; Goelz, S. E., et al. (1985) *Biochemical and Biophysical Research Communications* 130:118–126).

Example 3

This example demonstrates the accuracy of the Allele-specific Expression (ASE) assay.

Figure 1A:
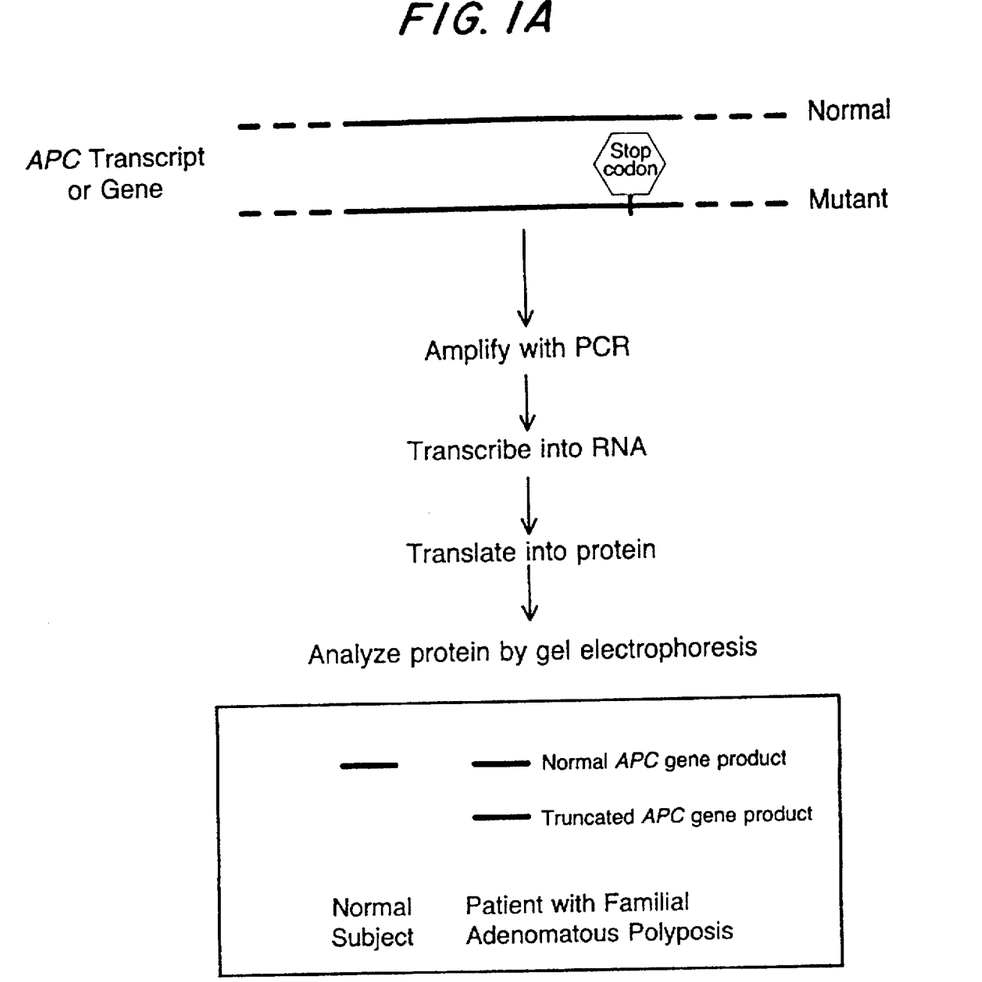
Figure 1B:
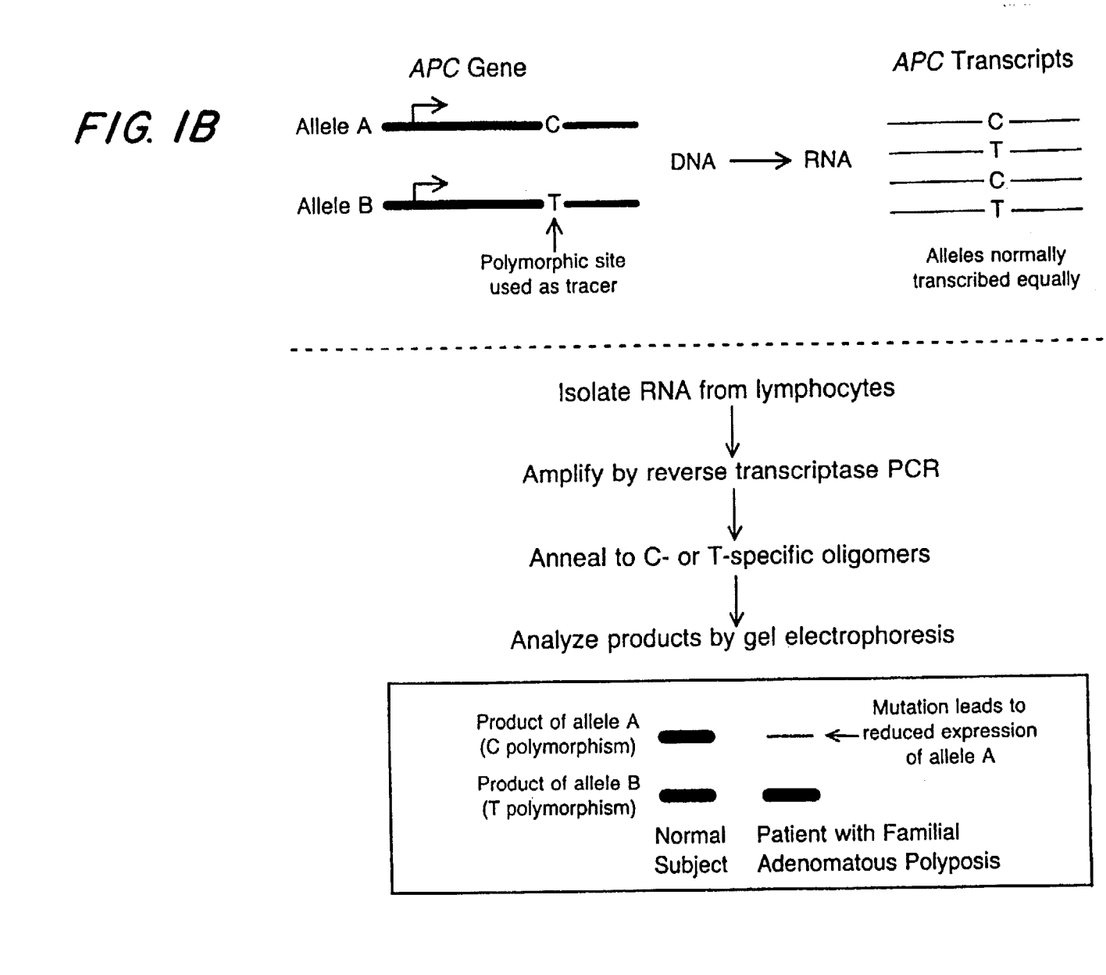

Considering that some cases of FAP might result from promotor or splicing mutations that lead to reduced levels of normal APC transcripts, we additionally addressed ways to easily identify such mutations. Because these cis acting mutations could at most result in a 50% decreased level of total transcript, we needed to devise a sensitive assay for expression of each of the two alleles individually. Therefore, we took advantage of single base pair polymorphisms to create an Allele-specific Expression (ASE) assay to detect this type of alteration (FIG. 1B). The accuracy of this assay was demonstrated in an allele mixing experiment.

Figure 4A:
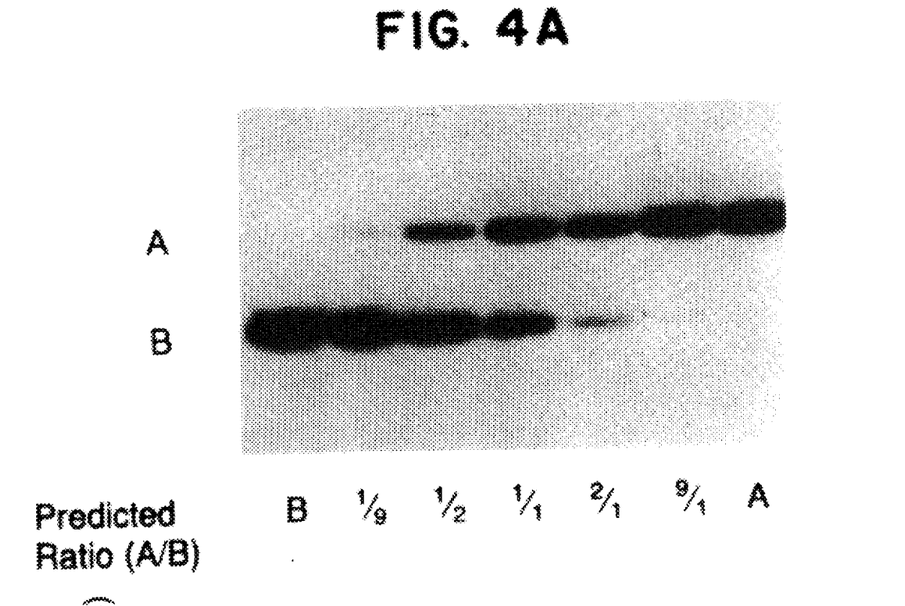
FIGS. 4A and 4B show allele mixing analysis of the ASE assay.
Figure 4B:
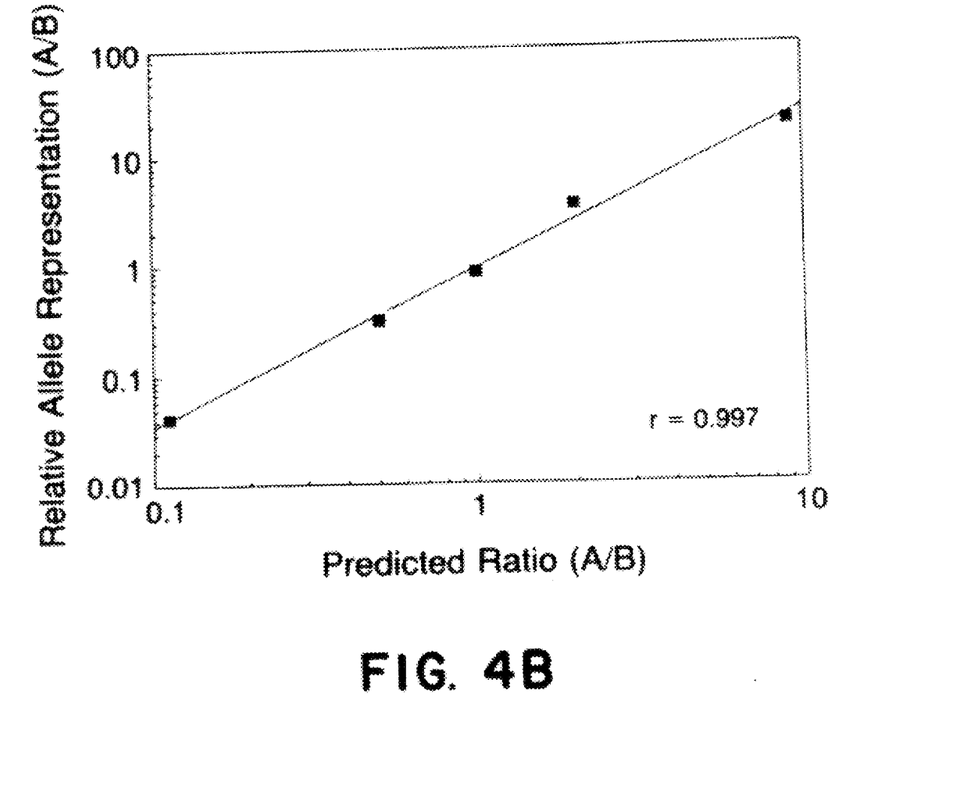

A controlled amount of RNA from two patients each homozygous for different alleles at the polymorphic site in exon 11 were mixed together in defined ratios, amplified, and analyzed by the ASE assay. Relative allele amounts determined by ASE analysis of these samples proved to be linear and quantitative with respect to the predicted ratios (r=0.997, FIG. 4).

Allele-specific Expression (ASE) Assay

The two site polymorphisms used in this assay were silent single base pair changes, one in exon 11 (codon 486, TAC/TAT) and one in exon 13 (codon 545, GCA/GCG) (Powell, S. M., et al. (1991) *Nature* 359:235–237). Homozygous cases were first sought by analyzing amplified APC exons 11 and 13 from genomic DNA.

Amplification of exon 11 and 13 was carried out using approximately 100 ng of genomic DNA, 350 ng each primer, and 2.5 units of Taq polymerase was used in a 50 µl Bind-Aid amplification kit (USB) reaction was cycled 35 times [30' denaturation (95° C.), 1' annealing (exon 11, 52.5° C.; exon 13, 55° C.) and 1' extension (70° C.)] All reactions included a 5' extension period at the end. The sequence of primers used for amplification were as follows: (exon 11, 5'-TAGATGATTGTCTTTTTCCTC-3' SEQ ID NO:13, 5'-TCATACCTGAGCTATCTTAAG-3' SEQ ID NO:14; exon 13, 5'-ACATGAAATTCATATTATAGTAC-3' SEQ ID NO:15, 5'-CTATTCTTACTGCTAGCATTA-3'. The genomic PCR product was added to a modified allele-specific ligation assay (Landgren, et al. supra, which is incorporated herein by reference). A common 9 base pair $^{32}$P-labeled oligomer and two different sized allele-specific oligomers (8 and 10 base pairs) were used in the ligation assay.

Specifically, one µl genomic PCR product was added to 2 ng of a common $^{32}$P-5' labeled oligomer (exon 11, 5'-GGGCTTACT-3' SEQ ID NO:17; exon 13, 5'-AGTGTTTTGA-3') SEQ ID NO:18) and 2 ng of allele-specific oligomers (exon 11, 5'-TGAAATGTAC-3' SEQ ID NO:19 and 5'-AAATGTAT-3'; SEQ ID NO:20; exon 13, 5'-GGTTATTGCA-3' SEQ ID NO:21 and 5'-TTATTGC G-3' SEQ ID NO:22) in a modified ligase-mediated reaction. Ligation products were separated through polyacrylamide/ 8M urea sequencing gels and the abundance of each allele was determined by the relative amount of allele-specific ligation product (17 bp for allele A, 19 bp for allele B, see FIG. 4). Quantitation was achieved with a PhosphorImager™ (Molecular Dynamics, Inc.). Segment 1 PCR products (derived from mRNA, as for the IVS protein assay) were then analyzed in the same quantitative ligation reaction to determine the relative abundance of APC transcripts expressed from each allele.

Example 4

This example demonstrates the use of the ASE assay to evaluate patients and healthy controls with no detectable protein abnormalities in the IVS assay.

Figure 5:
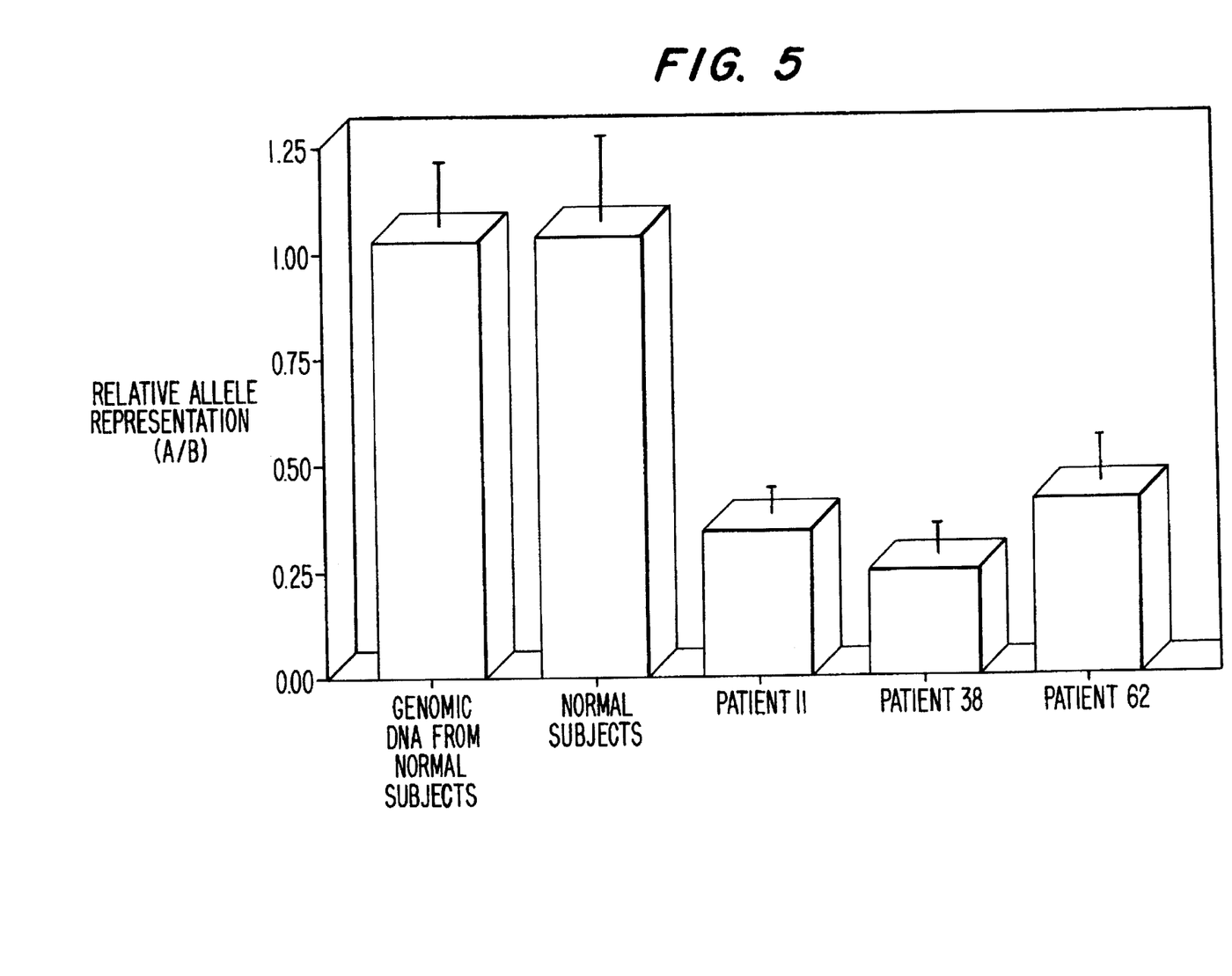
FIG. 5 shows detection of altered APC transcripts by the ASE assay.

We used the ASE assay to evaluate the eleven FAP patients without detectable APC protein abnormalities as well as nine healthy non-FAP controls. Seven patients and six normal individuals were heterozygous for at least one of the two polymorphisms and could thereby be analyzed. The relative allele ratio was 1+/−0.15 for all the genomic DNA samples (FAP or normal individuals) and for the RNA from control individuals. Three of the FAP patients had significantly reduced expression from one allele (FIG. 5). In each of these three cases, the ratio of allele abundance from expressed RNA template was significantly different from that of normal individuals and from the ratios found using genomic DNA instead of RNA as template (P<0.001, two tailed unpaired Student's t test). At least one other affected family member from the kindreds of these three patients was also analyzed and found to display similarly reduced expression of the same allele, demonstrating the expected inheritance.

Combined, these two assays (IVS protein and ASE) successfully identified APC mutations in 87% of the 62 different FAP kindreds tested.

We claim:

1. A method for detecting mutations in an APC gene, comprising the steps of:
   forming APC templates by amplifying some or all portions of APC gene coding sequences in a DNA sample of a human;
   making polypeptide products from said APC templates in in vitro transcription and translation reactions;
   analyzing said polypeptide products to determine the size of said polypeptide products, a truncated polypeptide product indicating a mutation in an APC gene in said DNA sample.

2. The method of claim 1 further comprising the steps of:
   determining whether the human is heterozygous for a polymorphism in the APC gene, a human who is heterozygous having a first and a second polymorphic allele of an APC gene;
   determining the relative amount of mRNA transcribed from each of said two polymorphic alleles in a DNA sample of a heterozygous human, a ratio of mRNA transcribed from said first allele to mRNA transcribed from said second allele which is greater than 1.2 or less than 0.8 indicating a mutation in one of said alleles in the DNA sample.

3. The method of claim 1 wherein the DNA sample is from a colorectal tumor.

4. The method of claim 1 wherein the DNA sample is from peripheral blood.

5. The method of claim 1 wherein the DNA sample is from prenatal or embryonic cells.

6. The method of claim 1 wherein the step of forming templates employs primers which introduce a promotor sequence for initiation of transcription and a sequence for translation initiation.

7. The method of claim 1 wherein the step of forming templates employs primers which introduce a T7 promotor sequence for initiation of transcription by T7 RNA polymerase.

8. The method of claim 1 wherein the step of forming templates employs primers having the sequences shown in SEQ ID NOS:1–10.

9. The method of claim 1 wherein the step of forming templates employs cDNA templates for amplifying exons 1–14 and genomic DNA for amplifying exon 15.

10. The method of claim 1 wherein the step of analyzing employs SDS-polyacrylamide gels to separate said polypeptide products on the basis of size.

11. The method of claim 2 wherein the polymorphism is a silent single base-pair change.

12. The method of claim 11 wherein the polymorphism is present in a codon selected from the group consisting of: codons 486, 545, 1493, 1756, 1960, 1678, and 2568.

13. The method of claim 2 wherein the presence of the polymorphism is determined by means of an allele-specific ligation assay.

14. The method of claim 2 wherein the relative amount of mRNA transcribed from each polymorphic allele is determined by means of an allele-specific ligation assay.

15. A method for detecting mutations in an APC gene, comprising the steps of:
   determining whether a human is heterozygous for a coding change silent polymorphism in the APC gene, a human who is heterozygous having a first and a second polymorphic allele of an APC gene;
   determining the relative amount of mRNA transcribed from each of said two polymorphic alleles in a DNA sample of a heterozygous human, a ratio of mRNA transcribed from said first allele to mRNA transcribed from said second allele which is greater than 1.2 or less than 0.8 indicating a mutation in one of said alleles in the DNA.

16. A method for detecting refutations in an APC gene comprising the steps of:
   determining whether a human is heterozygous for a silent single base-pair polymorphism in the APC gene, a human who is heterozygous having a first and a second polymorphic allele of an APC gene;
   determining the relative amount of mRNA transcribed from each of said two polymorphic alleles in a DNA sample of a heterozygous human, a ratio of mRNA transcribed from said first allele to mRNA transcribed from said second allele which is greater than 1.2 or than 0.8 indicating a mutation in one of said alleles in the DNA.

17. The method of claim 16 wherein the polymorphism is present in a codon selected from the group consisting of: codons 486, 545, 1493, 1756, 1960, 1678, and 2568.

18. The method of claim 15 wherein the presence of the polymorphism is determined by means of an allele-specific ligation assay.

19. The method of claim 15 wherein the relative amount of mRNA transcribed from each polymorphic allele is determined by means of an allele-specific ligation assay.

20. A method for detecting mutations in a gene of a human suspected of being a carrier of, or being affected by, a disease caused by mutation of the gene, the method comprising the steps of:

forming templates by amplifying some or all portions of the coding sequences of the gene in a DNA sample of a human;

making polypeptide products from said templates in in vitro transcription and translation reactions;

analyzing said polypeptide products to determine the size of said polypeptide products, a truncated polypeptide product indicating a mutation in the gene in said DNA sample.

21. The method of claim 20 further comprising the steps of:

determining whether the human is heterozygous for a polymorphism in the gene, a human who is heterozygous having a first and a second polymorphic allele of the gene;

determining the relative amount of mRNA transcribed from each of said two polymorphic alleles in a DNA sample of a heterozygous human, a ratio of mRNA transcribed from said first allele to mRNA transcribed from said second allele which is greater than 1.2 or less than 0.8 indicating a mutation in one of said alleles in the DNA.

22. A method of detecting mutations in a gene, comprising the steps of:

determining whether a human is heterozygous for a coding change silent polymorphism in the gene, a human who is heterozygous having a first and a second polymorphic allele of the gene, determining the relative amount of mRNA transcribed from each of said two polymorphic alleles in a DNA sample of a heterozygous human, a ratio of mRNA transcribed from said first allele to mRNA transcribed from said second allele which is greater than 1.2 or less than 0.8 indicating a mutation in one of said alleles in the DNA.

23. The method of claim 20, 21, or 22 wherein the gene is merlin, mutation of which is responsible for neurofibromatosis type 2.

24. The method of claim 20, 21, or 22 wherein the gene is VHL, mutation of which is responsible for von Hippel-Lindau disease.

25. The method of claim 20, 21, or 22 wherein the gene is CF, mutation of which is responsible for Cystic Fibrosis.

26. The method of claim 20, 21, or 22 wherein the gene is hMSH2, mutation of which is responsible for Hereditary Non-Polyposis colon Cancer (HNPCC).

27. The method of claim 21 or 22 wherein the presence of the polymorphism is determined by means of an allele-specific ligation assay.

28. The method of claim 21 or 22 wherein the relative amount of mRNA transcribed from each polymorphic allele is determined by means of an allele-specific ligation assay.

29. A method for detecting mutations in a gene, comprising the steps of:

determining whether a human is heterozygous for a silent, single base-pair polymorphism in the gene, a human who is heterozygous having a first and second polymorphic allele of the gene;

determining the relative amount of mRNA transcribed from each of said two polymorphic alleles in a DNA sample of a heterozygous human, a ratio of mRNA transcribed from said first allele to mRNA transcribed from said second allele which is greater than 1.2 or less than 0.8 indicating a mutation in one of said alleles in the DNA.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES

( x i ) SEQUENCE DESCRIPTION: SEQ ID NO:1:

```
GGATCCTAAT ACGACTCACT ATAGGGAGAC CACCATGGCT GCAGCTTCAT ATGATC          56
```

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES

( x i ) SEQUENCE DESCRIPTION: SEQ ID NO:2:

```
CTGACCTATT ATCATCATGT CG          22
```

( 2 ) INFORMATION FOR SEQ ID NO:3:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES

( x i ) SEQUENCE DESCRIPTION: SEQ ID NO:3:

```
GGATCCTAAT ACGACTCACT ATAGGGAGAC CACCATGGAT GCATGTGGAA CTTTGTGG          58
```

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES

( x i ) SEQUENCE DESCRIPTION: SEQ ID NO:4:

```
GAGGATCCAT TAGATGAAGG TGTGGACG                                    28
```

( 2 ) INFORMATION FOR SEQ ID NO:5:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES

( x i ) SEQUENCE DESCRIPTION: SEQ ID NO:5:

```
GGATCCTAAT ACGACTCACT ATAGGGAGAC CACCATGGTT TCTCCATACA GGTCACGG    58
```

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES

( x i ) SEQUENCE DESCRIPTION: SEQ ID NO:6:

```
GGAGGATCCT GTAGGAATGG TATCTCG                                     27
```

( 2 ) INFORMATION FOR SEQ ID NO:7:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES

( x i ) SEQUENCE DESCRIPTION: SEQ ID NO:7:

```
GGATCCTAAT ACGACTCACT ATAGGGAGAC CACCATGGAA AACCAAGAGA AAGAGGCAG   59
```

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES ( x i ) SEQUENCE DESCRIPTION: SEQ ID NO:8:

TTCACTAGGG CTTTTGGAGG C                                                                                          21

( 2 ) INFORMATION FOR SEQ ID NO:9:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES

( x i ) SEQUENCE DESCRIPTION: SEQ ID NO:9:

GGATCCTAAT ACGACTCACT ATAGGGAGAC CACCATGGGT TTATCTAGAC AAGCTTCG              58

( 2 ) INFORMATION FOR SEQ ID NO:10:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES

( x i ) SEQUENCE DESCRIPTION: SEQ ID NO:10:

GGAGTGGATC CCAAAATAAG ACC                                                                                        23

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES

( x i ) SEQUENCE DESCRIPTION: SEQ ID NO:11:

CAAGGGTAGC CAAGGATGGC                                                                                            20

( 2 ) INFORMATION FOR SEQ ID NO:12:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES

( x i ) SEQUENCE DESCRIPTION: SEQ ID NO:12:

TTGCTAGACC AATTCCGCG                                                                                             19

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (  i i  ) MOLECULE TYPE: DNA (genomic)

(  i i i  ) HYPOTHETICAL: YES (  x i  ) SEQUENCE DESCRIPTION: SEQ ID NO:13:

TAGATGATTG TCTTTTTCCT C                    21

( 2 ) INFORMATION FOR SEQ ID NO:14:

(  i  ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     (  i i  ) MOLECULE TYPE: DNA (genomic)

(  i i i  ) HYPOTHETICAL: YES

(  x i  ) SEQUENCE DESCRIPTION: SEQ ID NO:14:

TCATACCTGA GCTATCTTAA G                    21

( 2 ) INFORMATION FOR SEQ ID NO:15:

(  i  ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear     (  i i  ) MOLECULE TYPE: DNA (genomic)

(  i i i  ) HYPOTHETICAL: YES

(  x i  ) SEQUENCE DESCRIPTION: SEQ ID NO:15:

ACATGAAATT CATATTATAG TAC                  23

( 2 ) INFORMATION FOR SEQ ID NO:16:

(  i  ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     (  i i  ) MOLECULE TYPE: DNA (genomic)

(  i i i  ) HYPOTHETICAL: YES

(  x i  ) SEQUENCE DESCRIPTION: SEQ ID NO:16:

CTATTCTTAC TGCTAGCATT A                    21

( 2 ) INFORMATION FOR SEQ ID NO:17:

(  i  ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear     (  i i  ) MOLECULE TYPE: DNA (genomic)

(  i i i  ) HYPOTHETICAL: YES

(  x i  ) SEQUENCE DESCRIPTION: SEQ ID NO:17:

GGGCTTACT                                   9

( 2 ) INFORMATION FOR SEQ ID NO:18:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:18:

AGTGTTTTGA                          10

( 2 ) INFORMATION FOR SEQ ID NO:19:

( i ) SEQUENCE CHARACTERISTICS:
      ( A ) LENGTH: 10 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:19:

TGAAATGTAC                          10

( 2 ) INFORMATION FOR SEQ ID NO:20:

( i ) SEQUENCE CHARACTERISTICS:
      ( A ) LENGTH: 8 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:20:

AAATGTAT                            8

( 2 ) INFORMATION FOR SEQ ID NO:21:

( i ) SEQUENCE CHARACTERISTICS:
      ( A ) LENGTH: 10 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:21:

GGTTATTGCA                          10

( 2 ) INFORMATION FOR SEQ ID NO:22:

( i ) SEQUENCE CHARACTERISTICS:
      ( A ) LENGTH: 8 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:22:

```
TTATTGCG                                                                              8

( 2 ) INFORMATION FOR SEQ ID NO:23:

( i ) SEQUENCE CHARACTERISTICS:
           ( A ) LENGTH: 38 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:23:

GGATCCTAAT ACGACTCACT ATAGGGAGAC CACCATGG                                            3 8
```